United States Patent [19]

Fowles

[11] Patent Number: 4,836,397
[45] Date of Patent: Jun. 6, 1989

[54] CLOSURE FOR SEALING A PORT
[75] Inventor: Thomas A. Fowles, McHenry, Ill.
[73] Assignee: Baxter International Inc., Deerfield, Ill.
[21] Appl. No.: 670,502
[22] Filed: Nov. 13, 1984
[51] Int. Cl.⁴ .............................................. B65D 41/32
[52] U.S. Cl. .................... 220/214; 220/266; 220/356; 206/364; 604/111; 604/415
[58] Field of Search ................. 220/214, 356, DIG. 6, 220/359, DIG. 19, 266; 215/249, 250; 604/111, 404, 415, 408, 409, 410, 905; 206/306, 364; 138/96 R, 96 T; 313/59, 63, 65, 66, 904, 906

[56] References Cited

U.S. PATENT DOCUMENTS

| | | | |
|---|---|---|---|
| 2,705,336 | 4/1955 | Wilson | 138/96 T X |
| 2,734,649 | 2/1956 | Callahan et al. | 215/347 X |
| 3,203,545 | 8/1965 | Grossman | 206/364 X |
| 3,235,069 | 2/1966 | Bennett et al. | 220/356 X |
| 3,606,001 | 9/1971 | Talonn et al. | 206/364 |
| 3,978,859 | 9/1976 | Goodenough et al. | 604/111 X |
| 3,986,507 | 10/1976 | Watt | 128/214 D |
| 3,994,412 | 11/1976 | Difiglio | 604/111 X |
| 4,180,173 | 12/1979 | Diaz | 604/111 X |
| 4,295,495 | 10/1981 | Rosemeier et al. | 220/266 X |
| 4,335,756 | 6/1982 | Sharp et al. | 220/356 X |
| 4,415,393 | 11/1983 | Grimes | 604/415 X |

Primary Examiner—Steven M. Pollard
Attorney, Agent, or Firm—Paul C. Flattery; Robert H. Barrett; Paul E. Schaafsma

[57] ABSTRACT

A port and closure assembly is provided. The closure includes a cap that cooperates with the port to produce a friction fit. The cap and port are hermetically sealed together by a coating. The coating provides a method of determining if the closure has been opened.

17 Claims, 1 Drawing Sheet

CLOSURE FOR SEALING A PORT

BACKGROUND OF THE INVENTION

This invention relates to a closure for sealing a port of a container. In particular, the present invention relates to a tamper evident closure for hermetically sealing a port of a container.

Ports are utilized to provide a means of accessing material packaged within a container. As used herein, the term ports includes, without limitation, fitments, valves, and other means for accessing a container. Typically, the ports comprise a tubular structure with an inner bore. Located within the inner bore is a needle pierceable wall which provides a barrier between the fluid contained within the container and the outside environment. Usually a pointed means that pierces the pierceable wall is utilized to access the fluid and container. In the medical industry, parenteral and peritoneal dialysis solutions are packaged in flexible containers that are accessed through ports. An example of a flexible container utilized for parenteral solutions is the VIAFLEX ® collapsible plastic container sold by Travenol Laboratories, Inc. of Deerfield, Ill.

Particularly in the medical industry where these solutions are intended for intrabody administration, and in other applications, the solutions must be maintained in a sterile condition. In order to avoid introducing harmful agents into the body, it is essential that the solutions are maintained and extracted under sterile conditions. This requires not only that the container and its contents be in a sterile sealed condition at the time of receipt by the user, but also that no contamination to the contents occur when the container is opened by the physician or nurse prior to use. The problem of maintaining sterility is particularly acute at the port of the container. Any contamination that accumulates on the port may be introduced into the solution when the container is accessed.

To ensure an aseptic environment it is therefore necessary that the opening of the tubular bore of the port is sealed prior to use. Typically, the port is sealed by a closure. The closure should hermetically seal the port, remain affixed to the port during transit, and not be overly difficult to remove. Usually a doctor, nurse or other user of the container who must access the port, must be able to remove the closure with one hand. It is also advantageous if the closure provides a method of determining if the hermetic seal between the closure and the port has been broken. Providing a tamper evident closure is hampered by the fact that the closure should not be overly difficult to open. The prior art closures have not been entirely satisfactory in providing a hermetically sealed tamper resistant closure.

Because it is often necessary to utilize the solution contained in the container in an expedited manner, and in view of the fact that a misidentification can result in severe complications in the patient, it is advantageous if the container can be identified quickly. One way to accomplish this is to color code the closure. A disadvantage of color coding the closure is that once the closure is removed the container is no longer color coded.

Thus, it is a purpose of the present invention to overcome the disadvantages of the prior art.

SUMMARY OF THE INVENTION

The present invention provides a tamper evident closure that hermetically seals a port. The closure includes a cap that cooperates with the port to produce a friction fit. The cap and port are hermetically sealed together by a coating. The coating provides a method of determining if the closure has been opened. The coating may be color coded and provide a color coded band that remains on the port after the closure is removed.

Accordingly, one advantage of the present invention is that it provides a closure for hermetically sealing the opening of a port.

A further advantage of the present invention is that it provides a tamper evident closure for a port.

Another advantage of the present invention is that it provides a color coded closure for a port.

An additional advantage of the present invention is that it provides a color coded closure for a port that is constructed so that a color coded band remains on the port after the closure has been removed.

Moreover, an advantage of the present invention is that it provides a method for constructing a closure that hermetically seals a port.

Another advantage of the present invention is that it provides a method for constructing a tamper resistant closure.

Additional features and advantages are described in, and will be apparent from, the Detailed Description of the Presently Preferred Embodiments and from the drawings.

DETAILED DESCRIPTION OF THE PRESENTLY PREFERRED EMBODIMENTS

Figure 1:
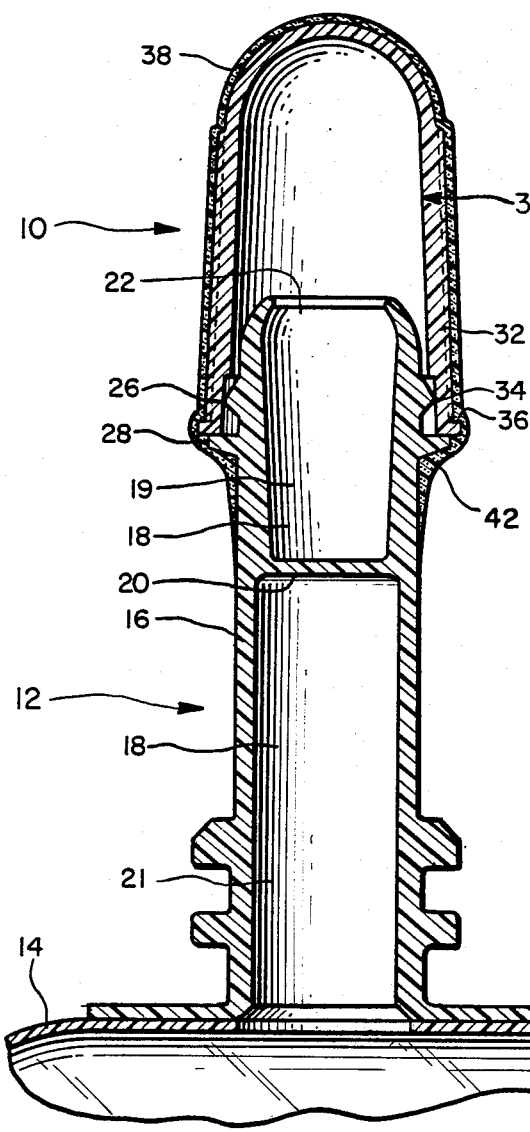
FIG. 1 illustrates a preferred embodiment of a closure and port of the present invention.

Referring to FIG. 1, the closure 10 of the present invention is illustrated. The closure 10 is designed to seal a port 12 that provides access to a container 14. The container 14 may be of any type known in the art, and typically is a flexible container made out of a plastic or like material. The container 14 usually contains a fluid that is accessed through the port 12.

The port 12 includes an outer wall 16 that defines a tubular bore 18. A partition wall 20 divides the tubular bore 18 into an upper bore 19 and lower bore 21. The upper bore 19 is in fluid communication with the outside environment, when the port 12 is not sealed, through an opening 22. The opening 22 allows the upper bore 19 to receive a needle or other access member that can pierce the partition wall 20 and thereby access the inner bore 21 and the container 14. The port 12 further includes ribs 26 and 28 that circumscribe the outer wall 16.

The closure 10 functions to seal the port 12 and specifically the opening 22. It is especially important in medical applications that this is a hermetic seal so that when the fluid within the container 14 is accessed for intravenous use the fluid is not contaminated with bacteria and other contaminants. It is also important that the closure 10 provide a means of determining if the closure has been opened and therefore the sterile environment violated.

The closure 10 includes a friction fitted cap 30. The friction fitted cap 30 includes a side wall 32 that extends to a bottom wall 34. The bottom wall 34 has a greater inner circumference than the side wall 32. As discussed in more detail below, this provides a cap 30 that cooperates with the port 12 to provide a friction fit. Extending from the bottom wall 34 is a flange member 36.

The cap 30 cooperates with the rib 26 of the port 12 to provide a friction fit. To this end, the inner circumference of the side wall 32 of the friction fitted cap 30 is less than the outer circumference of the rib 26, and the inner circumference of the bottom wall 34 is substantially the same as the outer circumference of the rib 26. As illustrated, when the cap 30 is positioned over the opening 22, the rib 26 and the bottom wall 34 cooperate to produce a friction fit between the cap 30 and the port 12.

In the preferred embodiment illustrated in FIG. 1, the port 12 includes a second rib member 28. The second rib member 28 has an outer circumference that is greater than the outer circumference of the first rib 26. The second rib 28 provides a base upon which the flange 36 and bottom wall 34 of the friction fitted cap 30 sit when the cap is frictionally fitted over the opening 22 of the port 12.

The closure 10 further includes a coating 38 that covers the cap 30 and a portion of the outer wall 16 of the port 12. The coating 38 ensures that a hermetic seal is present between the closure 10 and the port opening 22. Moreover, as discussed in detail below, the coating 38 functions to provide a tamper evident closure as well as a color coded closure 10.

Once the cap 30 is frictionally fitted over the opening 22 of the port 12, the coating 38 is applied over the cap 30 and a portion of the outer wall 16 of the port 12. To this end, the coating 38 covers the entire surface of the friction fitted cap 30 as well as at least a portion of the outer wall 16 of the port 12 located below the second rib 28.

The coating 38 may be color coded. To this end, the coating 38 may be blue, red, or any other color that designates to the industry or user a certain type of solution, e.g. plasma, saline, or dextrose solution. Thus, not only does the coating 38 ensure a hermetic seal between the closure 10 and the fitment 12, but it also provides a method for distinguishing different types of solutions.

Figure 2:
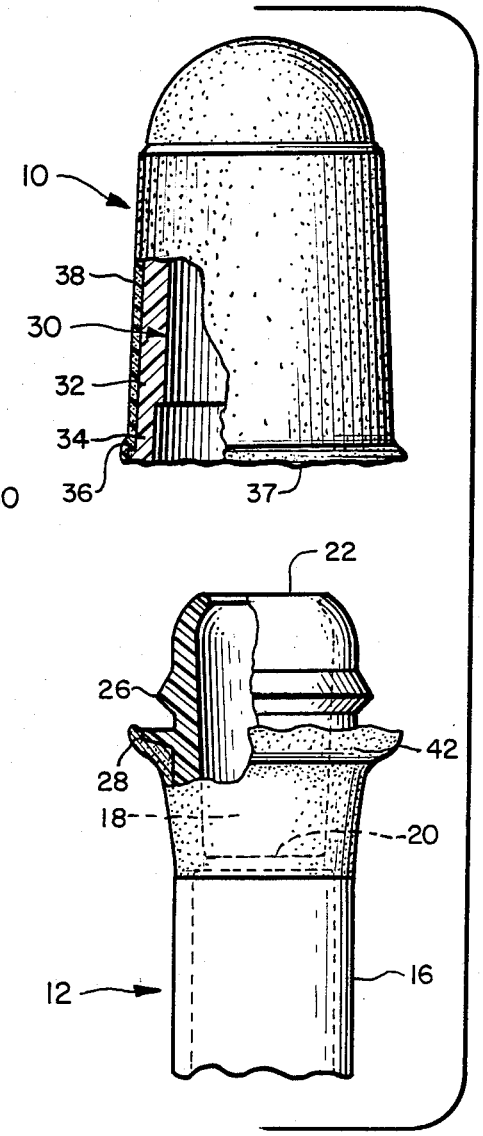
FIG. 2 illustrates a perspective view with parts broken away of the closure and port of FIG. 2.

As illustrated in FIG. 2, the coating 38 is designed to fracture upon the biasing of the closure 10 in a direction perpendicular to the port 12. Due to its construction, the coating 38 will fracture along a line 37 that circumscribes the flange 36 of the cap 30. The flange 36 acts as a stress riser in the coating 30 causing a uniform fracture along the line 37. Accordingly, once the closure 10 is removed from the port 12 a band 42 circumscribing a portion of the port 12 will remain. Thus, if the coating 38 is color coded, the port 12 will remain color coded even though the closure 10 has been removed.

Because the coating fractures along line 37, once the coating 38 is broken and therefore the closure 10 is opened, one is readily able to tell by visual inspection that the aseptic environment of the port 12 has been violated. Therefore, a tamper evident closure 10 for the port 12 is provided.

The coating 38 and friction fitted cap 30 are constructed so that they break away from the port 12 upon the exertion of a low removable force. Thus, the user, i.e. nurse or doctor, may easily remove the closure 10 from the port 12 with one hand.

The closure 10 and port 12 are hermetically sterilized by bulk radiation. It is also possible to make the parts so that the closure 10 and port 12 may be sterilized by steam sterilization or other sterilization techniques known in the art.

The coating 38 and cap 30 also function to provide a solid, smooth, and nontacky surface that cooperates well with the fitment attaching apparatus of packaging machines. Examples of such an apparatus is the heat seal press head that utilizes a walking beam in a form, fill, and seal packaging machine. Unless the port closure 10 has a relatively smooth and nontacky surface, it is possible for the closure 10 to get hung up in the heat seal press head slowing down or halting production.

Both the friction fitted cap 30 and the port 12 are injected molded. The friction fitted cap 30 is then snapped over the opening 22 of the port 12. The port 12 with friction fitted cap 30 is then dipped into a liquid plastic coating 38 and cured. The coating 38 may be air cured at ambient conditions. Once the plastic coating 38 cures, a hermetic seal is created around the cap 30 and the port 12. The closure 10 and port 12 may then be attached to the solution container 14. It is also possible to spray on the coating 38 or utilize a sputtering process.

The cap 30 is preferably created from polyethylene. The coating 38 is preferably an organic plasticsol or latex coating. It has been found that a coating 38 constructed from polyvinyl chloride functions well.

It should be understood that various changes and modifications to the preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A port and closure assembly for a solution container comprising:
    a port including an opening, a tubular bore, an outer wall defining the tubular bore, and a rib circumscribing the outer wall;
    a closure including a cap having an inner circumference substantially equal to the outer circumference of the rib of the outer wall of the port so that a friction fit is produced when the cap seals the opening of the port; and
    the closure further including a coating sealing the cap to the port.

2. The port and closure assembly of claim 1 wherein the port is hermetically sealed.

3. The port and closure assembly of claim 1 wherein:
    the port includes a second rib located below the first rib; and
    the cap sits on the second rib when it seals the opening of the port.

4. The port and closure assembly of claim 1 wherein the coating is color coded.

5. The port and closure assembly of claim 1 wherein the coating leaves a color coded band around the port after the closure is removed.

6. The port and closure assembly of claim 1 wherein the coating is constructed from an organic plasticsol.

7. The port and closure assembly of claim 3 wherein the coating extends along the port below the second rib of the outer wall.

8. A closure for a port having a tubular opening and a rib circumscribing an outer wall of the port comprising:
- a cap cooperating with the rib so that a friction fit is created when the cap covers the tubular opening of the port; and
- a coating for sealing the cap to the port, the coating providing means for determining if the closure has been opened.

9. The closure of claim 8 wherein the closure hermetically seals the port.

10. The closure of claim 8 wherein:
the port includes a second rib; and
the coating extends along the port below the second rib.

11. The closure of claim 10 wherein the cap sits on the second rib of the port.

12. The closure of claim 8 wherein the coating is so constructed and arranged that a band circumscribes the port after the closure is removed.

13. The closure of claim 11 wherein the band is color coded.

14. The closure of claim 8 wherein the coating is constructed from an organic plasticsol.

15. A closure for hermetically sealing a port having a tubular opening and at least one rib circumscribing an outer wall of the port comprising:
- a cap cooperating with a first rib so that a friction fit is created when the cap covers the tubular opening of the port;
- a coating for sealing the cap to the port; and
- the coating and cap cooperating to provide means for determining if the hermetic seal has been opened.

16. The closure of claim 15 including means for leaving a band around the port after the closure is removed from the port.

17. The closure of claim 16 wherein the band is color coded.

* * * * *

UNITED STATES PATENT AND TRADEMARK OFFICE
CERTIFICATE OF CORRECTION

PATENT NO. : 4,836,397

DATED : June 6, 1989

INVENTOR(S) : Thomas A. Fowles

It is certified that error appears in the above-identified patent and that said Letters Patent is hereby corrected as shown below:

In column 4, at line 51, after "port" add --, the coating covering at least a majority of an outer surface of the cap and at least a portion of the wall defining the tubular bore of the port--.

In column 5, at line 6, after "port," add --the coating covering the entire outer surface of the cap and a portion of the outer wall of the port,--.

In column 6, at line 14, after "port" add --, the coating covering the entire outer surface of the cap and a portion of the outer wall of the port--.

Signed and Sealed this

Twenty-seventh Day of March, 1990

Attest:

JEFFREY M. SAMUELS

*Attesting Officer*  *Acting Commissioner of Patents and Trademarks*